United States Patent [19]
Ghosal

[11] Patent Number: 6,153,198
[45] Date of Patent: Nov. 28, 2000

[54] WITHANIA SOMNIFERA COMPOSITION

[75] Inventor: Shibnath Ghosal, Varanasi, India

[73] Assignees: Natreon Inc., Highland Park, N.J.; Indian Herbs Research & Supply Company Ltd., Saharanpur, India

[21] Appl. No.: 09/351,890

[22] Filed: Jul. 13, 1999

[51] Int. Cl.$^7$ .................................................. A61K 35/78
[52] U.S. Cl. ......................................................... 424/195.1
[58] Field of Search ........................................ 424/195.1

[56] References Cited

U.S. PATENT DOCUMENTS 5,494,668  2/1996  Patwardhan .

OTHER PUBLICATIONS

"Anti–Stress Activity of Sitoindosides VII and VIII, New Acylsterylglucosides from Withania Somnifera", Phytother. Res. 1, 32–37 (1987) S.K. Bhattacharaya et al.
Immunomodulatory and CNS Effects of Sitoindosides IX and X, Two New Glycowithanolides from Withania Somnifera, Phytother. Res. 3, 201–206 (1989), S. Ghosal et al.
"Natural Products with Immunological Effects", Indian J. Indigenous Medicine 8, 1–7 (1991), S. Ghosal.
"Effects of Glycowithanolides from Withania Somnifera on Morphine–Induced Inhibition of Intestinal Motility and Tolerance to Analgesia in Mice", Phytother. Res. 9, 66–68 (1995), P. Ramarao et al.
"Effects of Glycowithanolides from Withania Somnifera on an Animal Model of Alzheimer's Disease and Preturbed Central Cholinergic Markers of Cognition in Rats", Phytother. Res. 9, 110–113 (1995).
"Antioxidant Activity of Glycowithanolides", Indian J. Exp. Biol. 35, 236–239 (1997), S. K. Bhattacharya et al.
"Systemic Administration of Defined Extracts from Withania Somnifera (Indian Ginseng) and Shilajit Differentially Affects Cholinergic but not Glutamatergic and Gabaergic Markers in Rat Brain", Neurochem. Int. 30, 181–190 (1997), R. Schleibs et al.
"Role of Withania Somnifera (Ashwagandha) in Various Types of Arthropathies", Indian J. Med. Res. 56, 1581–1583 (1968), N. P. Bector et al.

*Primary Examiner*—Francisco Prats
*Assistant Examiner*—Susan D. Coe
*Attorney, Agent, or Firm*—Walter Katz

[57] ABSTRACT

A high purity *Withania somnifera* extract composition in the form of a high purity, stable, free-flowing, light yellow-to-brown herbaceous powder, for producing an enhanced cognition effect for the user and to augment the learning facility in the geriatric population when taken in a dosage of 200–800 mg/day. This extract contains, by weight, (a) at least 3% of withanolide glycosides and sitoindosides, preferably 3–8%, (b) at least 3% of oligosaccharides, preferably 3–8%, preferably a molecular weight of <2000, and (c) less than 0.5% of free cytotoxic withaferin A (aglycone), wherein the ratio of (a):(c) is 75–95:25–5, and the ratio of (a):(b) is 40–60:60–40. An extraction process for obtaining such extract composition, and pharmaceutical and nutritional use products thereof, also are described.

13 Claims, No Drawings

WITHANIA SOMNIFERA COMPOSITION

BACKGROUND OF THE INVENTION

1. Field of the Invention

This invention relates to a composition of the plant *Withania somnifera*, and, more particularly to a high purity extract composition with advantageous levels of withanolides glycosides, sitoindosides and oligosaccharides, and substantially low levels of free withaferin A, which provides enhanced cognition-enhancing effects for the user, and an extraction process for obtaining such composition, as well as pharmaceutical and nutritional use products thereof.

2. Description of the Prior Art

The plant *Withania somnifera Dunn.* (Solanaceae), commonly known as Ashwagandha, has been used in herbal formulations of the Ayurvedic or Indian system of medicine to attenuate a cerebral function deficit in the geriatric population, and to augment the faculty of learning and memory to provide a non-specific host defense. These beneficial effects help the organism to ward off stress and act as an adaptogen. Ashwagandha also shows significant protection against pentylene tetrazole-induced seizures in experimental models of epilepsy, indicating its potential utility for treatment of petitmal epilepsy. Ashwagandha administration also produces a decrease in the core body temperature suggesting a reduced Body Merabolic Rate (BMR), enhanced body growth and increased longevity.

Typically, commercially available extracts of Ashwagandha obtained from old roots stock are either completely devoid of sitoindosides, or contain only traces of sitoindosides admixed with large amounts of toxic metabolites of withanolide aglycones, and polysaccharides, and wherein the polyoxygenated withasteroids are degraded during conventional extract prodecures. Moreover, admixture of several undetermined chemo-types of such wild-crafted Withania roots create further complications in respect of their chemical ingredients. For example, the Solanaceae alkaloids, i.e. the Withania family of the tropane-type, e.g. scopolamine, encountered in such Withania plant species, when present in the extract, causes adverse effects, particularly, amnesia, instead of the beneficent cognition-enhancing effect for which Ashwagandha is renowned. Cultivated withania roots also are devoid of any alkaloid (the Dragendorff-responsive spots is due to interaction with withanolide aglycones). Furthermore, high levels of polysaccharides are present in such commercially available *Withania somnifera* extracts which adversely affect the bioavailability of the active compounds present therein.

Accordingly, it is an object of this invention to provide a new and improved extract powder composition from selected *Withania somnifera* plants which contain advantageous proportions of those components which provide an optimum biological effect for the user.

Another object herein is to provide such an extract composition having defined amounts of withaferin glycosidic conjugates and oligosaccharides but with only little free cytotoxic withaferin A therein.

Yet another object of the invention is to provide a process for obtaining such *Withania somnifera* plant compositions by extracting selected *Withania somnifera* plant material immediately after harvesting, thereby to prevent hydrolysis of the withanolide glycosides/sitoindocides therein.

Still another object of the invention is to provide pharmaceutical and nutritional use products which include the extract composition of the invention.

A feature of the invention is the provision of a *Withania somnifera* plant extract composition having substantial amounts of sitoindosides and other withanolide glycosides, low molecular weight oligosaccharides, and particularly characterized by very low levels of cytotoxic withasteroid aglycones.

Another feature herein is to provide such an extract composition without inducing hybridization by cross-pollination which would reduce the number and content of withanolide glyosides and sitoindosides, and augment any biologically inactive high molecular weight polysaccharides.

These and other objects and features of the invention will be made apparent from the following more detailed description thereof.

SUMMARY OF THE INVENTION

What is described herein is a high purity *Withania somnifera* plant extract composition with substantially low levels of cytotoxic withaferin A (aglycone), in the form of a stable, free-flowing light yellow-to-brown herbaceous powder composition, which provides enhanced cognition and augmented learning facility in the geriatric population when taken in a dosage of about 200–800 mg/day. The biologically-enhancing composition of the invention includes, by weight, (a) at least 3% of withanolide glycosides and sitoindosides, preferably 3–8%, (b) at least 3%, preferably 3–8%, of oligosaccharides, preferably a mol. wt. of <2000, and (c) less than 0.5% of free withaferin A (aglycone), wherein the ratio of (a):(c) is 75–95:25–5 and the ratio of (a):(b) is 40–60:60–40. Preferably, the composition is at least 90% soluble, the ash content of this composition is less than 8%, and its moisture content is less than 5% (w/w).

The extract composition is obtained by (a) providing root stock of a *Withania somnifera* plant which is about 1 to 2 years old*, (b) extracting the root stock substantially immediately with an aqueous-alcoholic solvent, (c) concentrating the extract under vacuum, (d) treating the residue with an organic solvent to remove withanolide aglycones therefrom, (e) vacuum drying the insoluble residue below about 60° C. to provide a dry solid, and (f) pulverizing the solid under controlled temperature and humidity conditions.

* older roots contain undesired high molecular weight polymeric saccharides

In a specific aspect of the invention, the aqueous-alcoholic solvent is water-methanol or water-ethanol, preferably in a 1:1 ratio, and the organic solvent is chloroform or ethyl acetate.

DETAILED DESCRIPTION OF THE INVENTION

In accordance with the process of the invention, freshly harvested thin roots of *Withania somnifera* (Ashwagandha) obtained from steep rocks in the Himalaya mountains of India which is about 1–2 years old is coarsely crushed and then exhaustively extracted with hydroalcohol solvent e.g. a 1:1 mixture, at about 50–60° C. The aqueous-alcoholic extract then is concentrated under vacuum, and the concentrated extract is further treated with chloroform. The chloroform-insoluble residue therefrom is then vacuum dried below 60° C. to provide a dry extract, which is pulverized under controlled temperature and humidity conditions to form a fine powder.

The chloroform soluble-residual, which contains mainly cytotoxic withanolide aglycones and other constituents of the plant which do not contribute to the bioactivity of the Ashwagandha composition, is discarded.

The chloroform-insoluble/aqueous-soluble residue contains the desired withanolide glycoside and sitoindoside components which are potent bioactive constituents of Ashwagandha. The amount of such withasteroid glycosides therein, i.e. withanolide glycosides and sitoindosides, is determined on the basis of the withasteroid aglycones produced by subsequent hydrolysis of the chloroform-insoluble but aqueous soluble extract-fraction.

The resultant extract powder also contains desirable levels of oligosaccharides having a molecular weight of <2,000. Specifically, the water-soluble portion of this extract (see Table 1, column 2) contains 20 to 35% oligosaccharides, whereas commercially available extracts from other plants contain excessive amount, i.e. 90% of high molecular weight polysaccharides with only traces of oligosaccharides.

The compositions of this invention, and commercially available extracts of *Withania Somnifera*, are summarized and compared in Table 1 below.

TABLE 1

| Example/ Sample Description | Glycowithanolides (=Sitoindosides) and Polysaccarides[1] | Sitoindosides[2] | Withanolide Aglycone[3] | % Ratio of Sitoindosides and Aglycones |
|---|---|---|---|---|
| #1/IH-3581* | 15.19 | 8.16 | 2.04 | 80:20 |
| #2/IH-12762* | 10.28 | 4.37 | 0.82 | 84:16 |
| #3/IH-19383* | 11.63 | 2.34 | 0.10 | 95:05 |
| #4/IH-21744* | 12.12 | 6.06 | 1.32 | 81:19 |
| #5/IH-22615* | 19.40 | 5.41 | 1.20 | 82:18 |
| #6/Extract A+ | 22.32 | 0.10 | 0.88 | 10:90 |
| #7/Extract B+ | 8.44 | 0.08 | 1.22 | 06:94 |
| #8/Extract C+ | 5.33 | 0.04 | 2.02 | 02:98 |
| #9/Extract D+ | 11.77 | 0.17 | 1.88 | 06:94 |
| #10/Extract E+ | 14.33 | 0.002 | 0.59 | 04:96 |

*Extracts of present invention
+Commercially available extracts
[1]Water-soluble residue (%, w/w) containing oligosaccharides and polysaccharides*.
[2]Water-soluble, chloroform-insoluble residue (%, w/w in respect of root powder**).
[3]Chloroform-soluble residue***.

\* The compounds responded to both benzidine metaperiodate (for polyols) and Liebermann-Burchardt (for phytosteroids) reagents.
\*\* Sitoindosides were obtained by column chromatography to separate polysaccharides; characterization by high pressure thin layer chromatography (HPTLC) followed by acetylation and comprehensive spectroscopy.
\*\*\* Analyzed by HPTLC, preparative TLC, and comprehensive spectroscopy (proton nuclear magnetic resonance, mass spectroscopy, gas chromatograph-mass spectroscopy of silyl derivatives) using reference samples.

HPTLC Analysis of *Withania somnifera* Extracts

Withanolide glycosides/sitoindosides, the major bioactive constituents of *Withania somnifera*, are not readily identifiable in the HPTLC chromatographs (Track 1). However, upon carefully controlled hydrolysis, wherein they are converted into withanolide aglycones, they are readily observed in their HPTLC finger prints (Track 2). On the basis of such post-hydrolysis findings the presence and amounts of such withanolides/sitoindoside glycosides in the extract composition of the invention was determined. In contrast, commercially available *Withania somnifera* extracts (Track 3 and 4) lack these withanolide glycoside/sitoindoside component.

| Analytical and Chromatographic Conditions: | |
|---|---|
| Plate material: | Silica gel 60F254 |
| Solvent: | n-Butanol/Acetic acid/Water 4/1/2 |

-continued

| Analytical and Chromatographic Conditions: | |
|---|---|
| | (before hydrolysis) |
| | Chloroform/Methanol 90/10 |
| | (after hydrolysis) |
| Application mode: | Camag linomat IV |
| Development mode: | Twin Trough chamber |
| Detection wavelength: | 260 nm |

The withanolide aglycones are highly susceptible to rearrangement under acidic conditions.

EXAMPLE 1

(Track 1)

HPTLC Analysis of *Withania somnifera* Extract
(Present Invention, Before Hydrolysis)

| | Track 1 Analysis A: | | | | | | | |
|---|---|---|---|---|---|---|---|---|
| Peak | Start | | Max | | | End | | Area |
| # | mm | h | mm | h | [%] | mm | h | a | [%] |
| 1 | 13.4 | 74.8 | 13.8 | 148.8 | 26.07 | 16.6 | 0.3 | 1347.3 | 8.33 |
| 2 | 23.2 | 9.1 | 24.5 | 20.6 | 3.61 | 26.7 | 5.9 | 461.9 | 2.86 |
| 3 | 29.1 | 2.8 | 31.4 | 38.5 | 6.74 | 32.3 | 32.6 | 724.5 | 4.48 |
| 4 | 32.3 | 32.6 | 33.2 | 44.6 | 7.82 | 34.3 | 34.3 | 782.8 | 4.84 |
| 5 | 34.3 | 34.3 | 36.6 | 132.5 | 23.21 | 40.4 | 1.3 | 4788.8 | 29.62 |
| 6 | 41.0 | 0.1 | 43.5 | 28.7 | 5.03 | 47.7 | 0.4 | 845.5 | 5.23 |
| 7 | 54.5 | 1.0 | 57.1 | 37.6 | 6.60 | 59.2 | 15.9 | 1032.0 | 6.38 |
| 8 | 59.2 | 15.9 | 66.2 | 119.3 | 20.91 | 69.3 | 0.0 | 6185.9 | 38.26 |

Total height = 570.7
Total area = 16168.7

EXAMPLE 2

(Track 2)

HPTLC Analysis of *Withania somnifera* Extract
(Present Invention, After Hydrolysis)

| Track 2 Analysis B: | | | | | | | | |
|---|---|---|---|---|---|---|---|---|
| Peak | Start | | Max | | End | | Area | |
| # | mm | h | mm | h | [%] | mm | h | a | [%] |
| 1 | 13.2 | 0.0 | 13.8 | 345.7 | 17.92 | 16.4 | 17.5 | 4367.1 | 7.01 |
| 2 | 19.6 | 1.7 | 23.3 | 148.1 | 7.68 | 25.5 | 46.6 | 3992.5 | 6.41 |
| 3 | 26.4 | 46.6 | 30.8 | 638.4 | 33.09 | 35.5 | 70.3 | 25830.4 | 41.45 |
| 4 | 35.8 | 76.9 | 38.0 | 127.4 | 6.61 | 40.7 | 0.7 | 3888.4 | 6.24 |
| 5 | 40.7 | 0.7 | 44.5 | 366.9 | 19.02 | 48.6 | 24.7 | 13589.6 | 21.81 |
| 6 | 48.6 | 24.7 | 50.9 | 53.1 | 2.75 | 53.6 | 0.0 | 1539.3 | 2.47 |
| 7 | 53.8 | 0.9 | 58.9 | 111.5 | 5.78 | 62.1 | 31.9 | 4231.0 | 6.79 |
| 8 | 62.1 | 31.9 | 64.9 | 138.0 | 7.15 | 68.0 | 0.0 | 4883.0 | 7.84 |

Total height = 1929.1
Total area = 62321.3

EXAMPLE 3

(Track 3)

HPTLC Analysis of *Withania somnifera* Extract
(Commercial Extract, Before Hydrolysis)

| Track 3 Analysis C: | | | | | | | | |
|---|---|---|---|---|---|---|---|---|
| Peak | Start | | Max | | End | | Area | |
| # | mm | h | mm | h | [%] | mm | h | a | [%] |
| 1 | 12.1 | 2.4 | 13.0 | 106.3 | 28.42 | 16.0 | 10.3 | 1513.9 | 15.58 |
| 2 | 18.8 | 11.3 | 20.2 | 15.9 | 4.24 | 23.7 | 0.8 | 426.0 | 4.38 |
| 3 | 28.5 | 3.2 | 31.0 | 8.5 | 2.28 | 32.4 | 6.3 | 248.5 | 2.56 |
| 4 | 33.5 | 7.1 | 36.7 | 40.7 | 10.87 | 39.4 | 19.6 | 1599.8 | 16.46 |
| 5 | 39.9 | 19.8 | 42.3 | 53.1 | 14.19 | 43.8 | 36.2 | 1545.8 | 15.90 |
| 6 | 43.8 | 36.2 | 46.0 | 76.5 | 20.43 | 48.5 | 31.7 | 2514.0 | 25.87 |
| 7 | 49.1 | 32.2 | 50.6 | 39.8 | 10.62 | 53.3 | 1.0 | 1108.6 | 11.41 |
| 8 | 54.2 | 0.0 | 56.6 | 33.5 | 8.94 | 58.6 | 0.3 | 763.0 | 7.85 |

Total height = 374.1
Total area = 9719.6

EXAMPLE 4

(Track 4)

HPTLC Analysis of *Withania somnifera* Extract
(Commercial Extract, After Hydrolysis)

| Track 4 Ananlysis D: | | | | | | | | |
|---|---|---|---|---|---|---|---|---|
| Peak | Start | | Max | | End | | Area | |
| # | mm | h | mm | h | [%] | mm | h | a | [%] |
| 1 | 12.5 | 7.8 | 13.2 | 116.8 | 42.48 | 16.2 | 3.8 | 1593.1 | 30.01 |
| 2 | 25.5 | 1.4 | 27.5 | 13.7 | 4.96 | 30.4 | 3.2 | 352.4 | 6.64 |
| 3 | 32.9 | 4.7 | 34.5 | 11.7 | 4.25 | 36.6 | 0.3 | 264.7 | 4.99 |
| 4 | 37.2 | 1.7 | 40.0 | 88.9 | 32.33 | 42.2 | 14.7 | 2173.0 | 40.93 |
| 5 | 42.2 | 14.7 | 43.7 | 30.2 | 10.99 | 45.8 | 0.1 | 662.9 | 12.49 |
| 6 | 46.1 | 0.2 | 48.0 | 9.6 | 3.50 | 49.8 | 0.8 | 194.6 | 3.66 |

| Track 4 Ananlysis D: | | | | | | | | |
|---|---|---|---|---|---|---|---|---|
| Peak | Start | | Max | | End | | Area | |
| # | mm | h | mm | h | [%] | mm | h | a | [%] |
| 7 | 50.8 | 0.1 | 53.0 | 4.1 | 1.49 | 55.2 | 0.0 | 68.3 | 1.29 |

Total height = 275.0
Total area = 5308.9

The unique characteristics of the *Withania somnifera* extract composition of the invention are summarized in Table 2 below.

TABLE 2

| Withania Somnifera Extract Composition of Invention | |
|---|---|
| Appearance | Fine, free flowing, hygroscopic powder |
| Color | Light yellow to brown |
| Water soluble extractive value | Min 90.00% w/w |
| Total Withanolide glycosides and conjugates | Min 3% w/w (estimated as acetates), preferably 3–8% |
| Oligosaccharides (molecular weight <2000) | Min 3% w/w (estimated as acetates), preferably 3–8% |
| Free Withaferin A | Max 0.5% w/w |
| Ratio of Withanolide [glycosides and conjugates] to free withaferin A (aglycone) | 75-95:25-5 |
| Ratio of Withanolides To Oligosaccharides | 40-60:60-40 |
| Total ash content | Max 8.00% w/w |
| Moisture content | Max 5.00% v/w |
| Dosage | 200–800 mg per day |

Pharmaceutical and Nutritional Formulas

Representative pharmaceutical and nutritional use products which include the *Withania somnifera* extract composition of the invention are given in Examples 5–11 below.

EXAMPLE 5

Tablets and Capsules

| Ingredient | Composition (w/w, in %) | Quantity per Tablet (mg) |
|---|---|---|
| 1. Withania Somnifera extract | 60.0 | 250.0 |
| 2. Avicel pH 101 | 20.0 | 84.0 |
| 3. Starch 1500 | 17.5 | 75.5 |
| 4. Stearic acid, N.F. (powder) | 2.0 | 8.5 |
| 5. Cab-O-Sil | 0.5 | 2.0 |

*Withania somnifera* extract is granulated with starch paste to make a free-flowing powder. Blend all the ingredients, except 4, for 25 min. in a blender. Screen in 4 and blend for an additional 5 min. Compress into tablets using 7/16-in standard concave tooling. Alternately, the blended material can be filled into appropriate capsules.

EXAMPLE 6

Chewable Tablets

| Ingredient | Composition (w/w, in %) | Quantity per Tablet (mg) |
| --- | --- | --- |
| 1. Withania Somnifera extract | 12.26 | 27.60 |
| 2. Sodium ascorbate, USP | 36.26 | 81.60 |
| 3. Avicel pH 101 | 17.12 | 38.50 |
| 4. Sodium saccharin, (powder), N.F. | 0.56 | 1.25 |
| 5. DiPac | 29.30 | 66.00 |
| 6. Stearic acid, N.F. | 2.50 | 5.60 |
| 7. Imitation orange Flavor | 1.0 | 2.25 |
| 8. FD & C Yellow #6 dye | 0.5 | 1.12 |
| 9. Cab-O-Sil | 0.5 | 1.12 |

Blend all the ingredients, except 6, for 20 min in a blender. Screen in 6 and blend for an additional 5 min. Compress into tablets using 7/16-in standard concave tooling.

EXAMPLE 7

"Maintenance" Multivitamin Tablets or Capsules

| Ingredient | Composition (w/w, in %) | Quantity per Tablet (mg) |
| --- | --- | --- |
| 1. Withania Somnifera extract, free-flowing | 33.25 | 66.50 |
| 2. Vitamin A acetate (dry form 500 IU and 500 $D_2$ per mg) | 5.5 | 11.0 |
| 3. Thiamine mono-nitrate, USP | 0.8 | 1.65 |
| 4. Riboflavin, USP | 1.1 | 2.10 |
| 5. Pyridoxine HCl, USP | 1.0 | 2.10 |
| 6. 1% Cyanocobalamine (in gelatin) | | |
| 7. D-Calcium pantothenate, USP | 3.75 | 7.50 |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid, (powder), N.F. | 1.5 | 3.00 |
| 13. Magnesium stearate, (powder), N.F. | 1.0 | 2.00 |

Blend all ingredients for 20 min in a suitable blender. Screen in 12 and blend for an additional 5 min. Compress at a tablet weight of 200 mg using 3/8-in standard concave tooling. Alternately, blended material is filled into a capsule containing 200 mg of multi-vitamins. These tablets or capsules can be used as nutritional supplements.

EXAMPLE 8

Geriatric Formula Vitamin Tablets

| Ingredient | Composition (w/w, in %) | Quantity per Tablet (mg) |
| --- | --- | --- |
| 1. Withania Somnifera extract free-flowing powder | 17.45 | 96.00 |
| 2. Ferrous sulfate, USP 95% Ethecal granulation | 15.00 | 78.00 |
| 3. Thiamine mono-nitrate; USP | 1.09 | 6.00 |
| 4. Riboflavin, USP | 1.00 | 5.50 |
| 5. Niacinamide, USP | 6.00 | 33.00 |
| 6. Ascorbic acid USP fine crystal | 15.00 | 78.00 |
| 7. Calcium pantothenate, uSP | 0.73 | 4.00 |
| 8. Pyridoxine HCl, USP | 0.14 | 0.75 |
| 9. Cyanocobalmine, 0.1% spray dried | 0.82 | 4.50 |
| 10. AcDisol | 2.00 | 11.00 |
| 11. Stearic acid, (powder),N.F. | 2.00 | 11.00 |
| 12. Magnesium stearate, (powder), N.F. | 0.25 | 1.38 |
| 13. CeloCat | 38.52 | 211.87 |

Prepare a premix of items 2, 3, 6, 7. Mix in other ingredients except 10 and 11 and blend for an additional 5 min. Compress using oval punches (1=0.480 in., w=0.220× cup=0.040 in.) Sugar or film coat. These tablets can be used as nutritional supplements.

EXAMPLE 9

Elixir Formula

| Ingredient | Quantity |
| --- | --- |
| 1. Withania Somnifera Extract | 0.2 g |
| 2. Lemon Tincture | 5.0 ml |
| 3. Orange Tincture | 5.0 ml |
| 4. Sodium Saccharin | 0.5 g |
| 5. Propylene Glycol | 65.0 ml |
| 6. Glycerine | 15.0 ml |
| 7. Sorbitol, USP, sufficient quantity to make | 100.0 ml |

Dissolve 1 in 5 and 6 which have been heated to 50° C. Dissolve 4 in 2 and 3 and add the solution of *Withania somnifera* extract at 25° C. Add sufficient sorbitol to make the product measure 100 ml.

EXAMPLE 10

Elixir Formula

| Ingredient | Quantity |
| --- | --- |
| 1. Withania Somnifera Extract | 0.4 g |
| 2. Orange oil | 0.1 ml |
| 3. Benzaldehyde | 0.005 ml |
| 4. Sorbitol Solution USP | 10.0 ml |
| 5. Propylene Glycoi | 40.0 ml |
| 6. Alcohol | 40.0 ml |
| 7. Purified Water, sufficient quantity to make | 100.0 ml |

Dissolve 1 in 4 and 5 which have been heated to 50° C. Add 2 and 3 to the alcohol and mix with 1 at 25° C. Add sufficient water to make the product measure 100 ml.

EXAMPLE 11

Colloidal Magnesium Aluminum Premix (5% Fully Hydrated Magma)

| Ingredient | Quantity |
| --- | --- |
| 1. Colloidal magnesium aluminum silicate | 5.0% w/v |
| 2. Methyl paraben | 0.12% w/v |
| 3. Propyl paraben | 0.03% w/v |
| 4. Water, qs | 100% |

A. The parabens are dissolved in approximately 60% of the purified water at 90° C.
B. The colloidal magnesium aluminum silicate is slowly added to step A and maintained at 90° C. for one hour with gentle agitation.
C. The premix is cooled to 40° C. and passed through a colloid mill or homogenizer (2500 psi) rinsing through with fresh purified water.
D. The premix is brought to final volume with purified water and agitation.
E. The premix may be stored in suitable containers at room temperature for several months or more.

EXAMPLE 11A

Oral Suspension

| Ingredient | Quantity |
| --- | --- |
| 1. Withania Somnifera Extract | 0.3% w/v |
| 2. Colloidal magnesium aluminum silicate premix (5% formula 21) | 20.0% w/v |
| 3. Poloxamer 331 | 0.05% w/v |
| 4. Glycerin | 10.0% w/v |
| 5. Potassium sorbate | 0.2% w/v |
| 6. Sodium benzoate | 0.1% w/v |
| 7. Colorant | qs |
| 8. Flavor | qs |
| 9. Liquid sugar (sp. Gr = 1.33) | 65.0% |
| 10. Citric acid or sodium hydroxide to pH 5.5 | qs |
| 11. Purified water, qs | 100% |

1. Dissolve potassium sorbate, sodium benzoate, colorant in aqueous glycerin.
2. Add liquid sugar colloidal magnesium aluminum silicate premix and half the poloxamer 331 and sulfa drug in step 2 with agitation.
3. Disperse the rest of the poloxamer 331 and sulfa drug in step 2 with agitation.
4. 4. Add flavor to step 3 and pass the suspension through a colloid mill or homogenizer rinsing through with purified water.
5. Adjust pH to 5.5 with either citric acid or sodium hydroxide solution.
6. Add purified water to final volume.

EXAMPLE 12

Improved Bioactivity in the Presence of Oligosaccharides

Test Protocol:

Ehrlich Ascites tumor (s-180, $1 \times 10^6$ cells, all viable), suspended in phosphate buffer saline (PBS, 0.5 ml), were inoculated (i.p.) to a group of adult mice. After 2 h, withaferin-A (WA) (2.5 mg/100 g b.w.) and withanolide+ oligosaccharides (1:10 w/w) were administered to Group-2 and Group-3 animals (Table 3). The control (Group 1) received only the vehicle (PBS) following the tumor inoculation. On day-10, the tumor cells were removed from the peritoneal cavity and the viable and dead cells were enumerated microscopically using the dye-exclusion method.

Effect of Withaferin A on the Viability and Growth of S-180 Tumor Cells

TABLE 3

| Group[a]/Treatment | Tumor cells $\times 10^7$ Viable Cells | ±SD Dead Cells |
| --- | --- | --- |
| 1. PBS (Control) | 12.14 ± 3.04 | 0.80 ± 0.04 |
| 2. Withaferin A (WA) | 8.49 ± 2.15 | 5.17 ± 1.97 |
| 3. Withaferin-A + Oligosaccharides (1:10) | 3.03 ± 0.92 | 0.72 ± 0.05 |

[a]12-week-old Swiss mice; n = 10 in each group; WA, withaferin-A: and withaferin-A + oligosaccharides of *W. somnifera* were administered.

The results in Table 3 suggest that the anti-tumor activity of Group 3 withaferin A+oligosaccharides (1:10), unlike that of WA, was not due to cytotoxicity common to anti-tumor drugs, but due to immunomodulation (Ghosal et al., Phytother. Res., 5, 201–206, 1989). This postulate is supported by the decreased tumor growth and only a marginal increase in the number of dead cells compared to the control group. By contrast, the WA group elicited less effective tumor control compared to Group-3 and an appreciable number of dead cells.

Thus, the oligosaccharide carrier Group 3 in the extract composition of the invention can significantly modify the nature and extent of the bioactivity of withaferin-A (WA).

In summary, the *Withania somnifera* extract composition of the invention includes an advantageous combination of components in defined amounts and proportions for optimum biological activity. Particularly, the sitoindoside constituent therein produces an immunostimulation response as reflected by activation of peritoneal macrophages, phagocytosis, and increased activity of lysomal enzymes secreted by activated macrophages. The substantial absence of withasteroid aglycones therein precludes the adverse cytotoxic effect observed with other related compositions in the art. The defined amount and kind of oligosaccharides in the extract composition of the invention also plays a very important role in the bioavailability of the *Withania sominifera* active principles. Specifically, the combination of such oligosaccharides without Withanolide aglycones elicits a desirable immunostimulatory effect for the user.

While the invention has been described with particular reference to certain embodiments thereof, it will be understood that changes and modifications may be made which are within the skill of the art. Accordingly, it is intended to be bound only by the following claims, in which:

What is claimed is:

1. A *Withania somnifera* extract composition, in the form of a stable, herbaceous powder, which produces a cognition effect and learning facility for the user, when taken in a dosage of about 200–800 mg/day, which comprises, by weight, (a) at least 3% of withanolide glycosides and sitoindosides, (b) at least 3% of oligosaccharides, and (c) less than 0.5% of free withaferin A (aglycone), wherein the weight ratio of (a):(c) is 75–95:25–5, and the weight ratio of (a):(b) is 40–60:60–40.

2. A composition according to claim 1 wherein the oligosaccharides have a molecular weight of less than 2,000.

3. A composition according to claim 2 including ash wherein said extract composition is at least 90% water soluble, the ash content is a maximum of 8%, and its moisture content is maximum of 5% (w/w).

4. A composition according to claim 1 wherein (a) is 3–8%, and (b) is 3–8%.

5. A process of making the extract composition of claim 1 which comprises (a) providing root stock of a *Withania somnifera* plant which is about 1–2 years old, (b) extracting said root stock with an aqueous-alcoholic solvent, (c) concentrating the extract under vacuum, (d) treating the residue with an apolar organic solvent to remove free withanolide A aglycones therefrom, (e) vacuum drying the insoluble residue of such treatment below about 60° C. to provide a dry solid, and (f) pulverizing the solid under controlled temperature and humidity conditions, to obtain the desired powder product.

6. A process according to claim 5 wherein said aqueous-alcoholic solvent is water-methanol or water-ethanol, and said organic solvent is chloroform or ethyl acetate.

7. A pharmaceutical or nutritional product which includes the extract composition of claim 1.

8. A product according to claim 7 in which said extract is present in a dosage form suitable for oral administration.

9. A product according to claim 8 wherein said dosage level is about 200 to 800 mg/day.

10. A product according to claim 8 which includes excipients suitable for such oral administration.

11. A product according to claim 8 wherein the dosage form is a tablet.

12. A product according to claim 8 wherein said dosage form is a capsule.

13. A product according to claim 8 wherein said dosage form is an elixir or suspension.

* * * * *